(12) United States Patent
Knöller et al.

(10) Patent No.: US 11,752,126 B2
(45) Date of Patent: Sep. 12, 2023

(54) STABLE CANNABINOID COMPOSITIONS

(71) Applicant: Sino-German M&A Service GmbH, Frankfurt am Main (DE)

(72) Inventors: Ilse Knöller, Grevenbroich (DE); Thomas Sowik, Düsseldorf (DE)

(73) Assignee: Sino-German M&A Service GmbH, Frankfurt am Main (DE)

( * ) Notice: Subject to any disclaimer, the term of this patent is extended or adjusted under 35 U.S.C. 154(b) by 241 days.

(21) Appl. No.: 16/628,865

(22) PCT Filed: Jul. 6, 2018

(86) PCT No.: PCT/EP2018/068452
§ 371 (c)(1),
(2) Date: Jan. 6, 2020

(87) PCT Pub. No.: WO2019/008179
PCT Pub. Date: Jan. 10, 2019

(65) Prior Publication Data
US 2020/0237713 A1    Jul. 30, 2020

(30) Foreign Application Priority Data

Jul. 7, 2017 (EP) .................................... 17180380

(51) Int. Cl.
*A61K 31/352* (2006.01)
*A61K 31/05* (2006.01)

(52) U.S. Cl.
CPC ............ *A61K 31/352* (2013.01); *A61K 31/05* (2013.01)

(58) Field of Classification Search
CPC ................................................... A61K 31/352
See application file for complete search history.

(56) References Cited

U.S. PATENT DOCUMENTS

| | | | |
|---|---|---|---|
| 2008/0045559 A1 | 2/2008 | Zhang et al. | |
| 2015/0045282 A1 | 2/2015 | Elsohly et al. | |
| 2016/0081976 A1* | 3/2016 | Bromley | A61K 2300/00 424/456 |

FOREIGN PATENT DOCUMENTS

| | | |
|---|---|---|
| JP | H09-510712 A | 10/1997 |
| JP | 2007-508296 A | 4/2007 |
| JP | 2010-506886 A | 3/2010 |
| WO | 95/25504 A1 | 9/1995 |
| WO | 00/71163 A1 | 11/2000 |
| WO | 03/074027 A2 | 9/2003 |
| WO | 2004/105694 A2 | 12/2004 |
| WO | 2007/016175 A1 | 2/2007 |
| WO | 2007/016176 A2 | 2/2007 |
| WO | 2008/046905 A1 | 4/2008 |
| WO | 2012/050978 A1 | 4/2012 |
| WO | 2013/009928 A1 | 1/2013 |
| WO | 2014/165672 A1 | 10/2014 |
| WO | WO-2014165672 A1 * | 10/2014 ........... A61K 31/337 |

OTHER PUBLICATIONS

Mecha, M., et al. "Cannabidiol provides long-lasting protection against the deleterious effects of inflammation in a viral model of multiple sclerosis: A role for A2A receptors." Neurobiology of Disease. (2013), vol. 59, pp. 141-150. (Year: 2013).*
Written Opinion of the International Searching Authority of PCT/EP2018/068452 dated Sep. 19, 2018.
International Search Report of PCT/EP2018/068452 dated Sep. 19, 2018.
Madaswamy S. Muthu et al., "Development of docetaxel-loaded vitamin E TPGS micelles: formulation optimization, effects on brain cancer cells and biodistribution in rats", Nanomedicine, Mar. 1, 2012, vol. 7, No. 3, pp. 353-364 (12 pages total).

* cited by examiner

*Primary Examiner* — John S Kenyon
(74) *Attorney, Agent, or Firm* — Sughrue Mion, PLLC

(57) ABSTRACT

A composition comprising a cannabinoid, in particular a phytocannabinoid or a synthetic cannabinoid, where the cannabinoid is stabilised against oxidation and/or photochemical degradation, characterized in that the composition comprises a micellar solution of composite micelles in an aqueous solution and where the composite micelles encapsulate the cannabinoid.

7 Claims, 1 Drawing Sheet

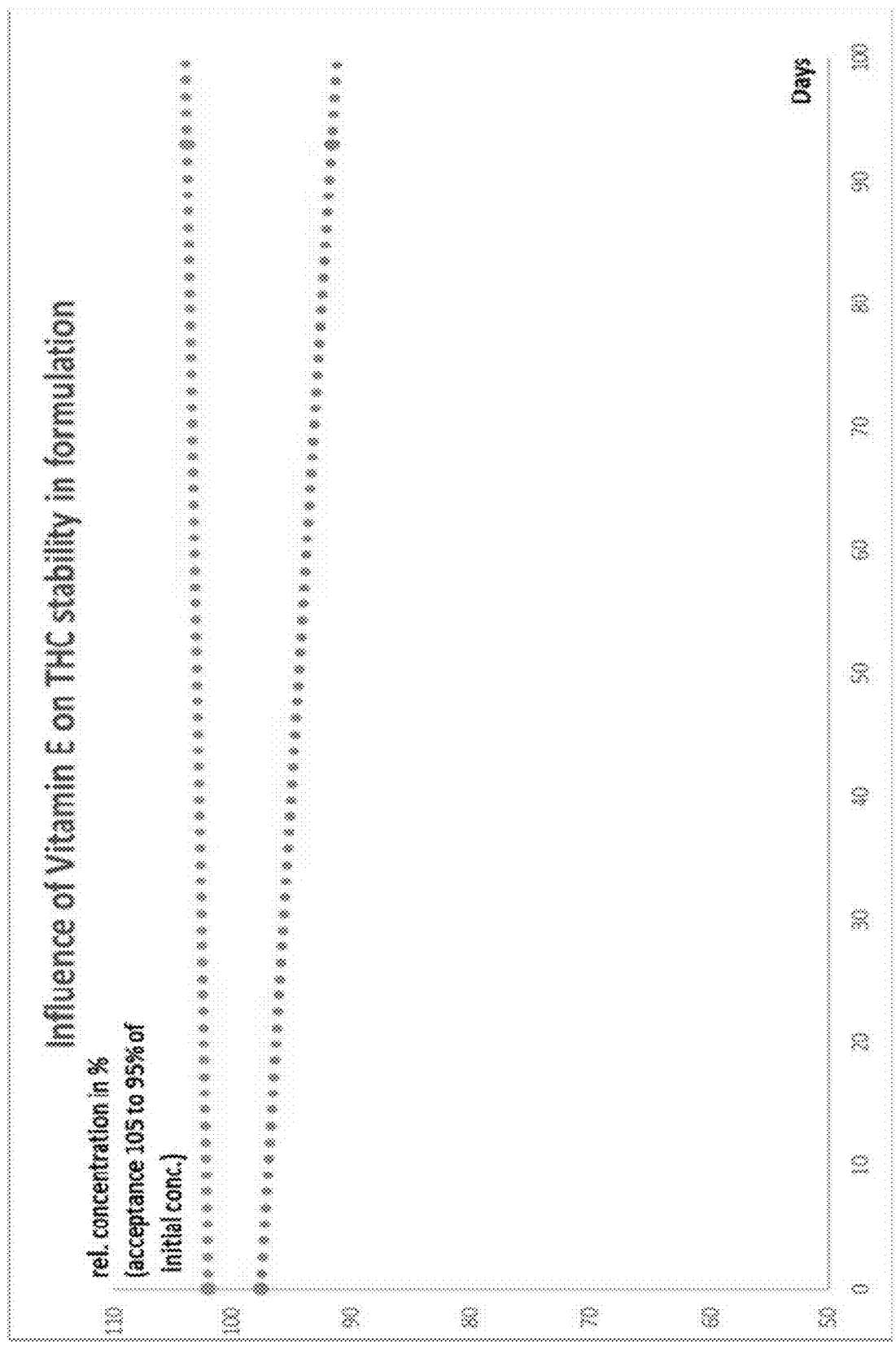

STABLE CANNABINOID COMPOSITIONS

TECHNICAL FIELD

The present invention relates to compositions comprising lipophilic bioactive compounds such as a cannabinoid in which the cannabinoid is stabilized against oxidation and/or photochemical degradation.

PRIOR ART

Pharmaceutical formulations allow active ingredients to enter the body and arrive at the targeted tissue so that they may develop the intended effect there. When an active ingredient has to be administered via a given route, much consideration should be given to the physico-chemical properties of the active ingredient and its formulation.

For instance, the uptake of an active ingredient by the intestinal tract via an oral route, i.e. the ability to enter the systemic circulation, is heavily dependent of its stability towards acids (gastric juice), enzymatic degradation (e.g. pancreatic enzymes) and water solubility.

Also, the uptake via the skin depends on the ability of the active ingredient to bypass the upper skin layer consisting of the upper epidermis with its skin cells and fibers without blood and lymph vessels, the lower dermis and into the subcutaneous environment with its blood vessels.

In the intestinal tract, lipophilic compounds are made water-soluble by the help of the bile salts, which have amphiphilic properties. With the help of the bile salts the lipophilic components are caged in small round shaped structures, so-called micelles, which consist of an inner lipophilic and outer water-soluble moiety and thus can render lipophilic ingredients, which are a priori water insoluble, water-soluble.

However, the endogenous processes have a relatively low efficacy. They need most often stimulation of the release of the bile salts from the gall bladder by the lipophilic compound itself and stimulation by concomitant food intake. The efficacy depends on the regular motility of the intestinal tract to bring the ingredients into contact with the bile salts to form an emulsion, as well as the amount of bile salts that can be released.

Usually, this process increases the uptake of lipophilic compounds up to 5-15% bioavailability, which is sufficient for supply in healthy, young adults. In diseased or elderly persons the regular processes may, however, not be sufficient to exert the desired effect of an active ingredient or maintain health and wellness, e.g. due to hypovitaminoses of vitamin A, D, E, and K and other essential factors such as ubiquinol/ubiquinone, or essential fatty acids. Moreover, natural extracts from fruits or vegetables which often have lipophilic or resin-like instable constituents may not be taken up anymore.

Many processes to emulsify these ingredients are described in the literature and have been used for many years. However, these emulsions may have also low efficacy due to their instability in the intestinal tract, in which the emulsion may "break" due to dilution below critical micelle concentration and thereby rendering the micellar formulations instable.

The above-mentioned problems are further exacerbated in liquid or gel-like formulations which in most cases display insufficient shelf life, since degradation of the ingredient to be emulsified in response to light and oxygen exposure further reduces the availability of ingredients in an emulsion, when compared to solid forms such as lozenges or capsules.

Cannabinoids exhibit low solubility and stability in aqueous solutions and are therefore often formulated as oily solutions or dissolved in organic solvents which are unsuitable for ingestion or topical application. When formulated as oily solution or dissolved in organic solvents, the cannabinoids suffer from both oxidative and photochemical degradation, which quickly becomes analytically detectable.

Therefore there is a need to provide formulations of otherwise instable, lipophilic active ingredients which exhibit improved stability of the ingredient when passing through the gastro-intestinal tract and which moreover display excellent shelf life, especially when exposed to irradiation, temperature variations and or sunlight.

SUMMARY OF THE INVENTION

The compositions, as well as the process for obtaining such compositions, according to the present invention, provide for a means to formulate active ingredients, in particular lipophilic or resinous active ingredients such as cannabinoids, in way that they are readily available throughout the entire gastro-intestinal tract with high efficiency and moreover display enhanced stability against light and/or thermal degradation when compared with compositions according to the state of the art by encapsulating the cannabinoid in micelles of non-aqueous non-alkoxylated solvent and/or in composite micelles of non-aqueous alkoxylated compounds and non-aqueous non-alkoxylated compounds such as TPGS/tocopherol composite micelles. This allows to provide formulations that can easily be stored under ambient conditions without special precautions which would otherwise be needed for compositions according to the state of the art. In particular, the formulations do not need to be refrigerated and/or kept in the dark.

It is an object of the present invention to provide a composition comprising a lipophilic bioactive compound such as a cannabinoid, in particular a phytocannabinoid or a synthetic cannabinoid, where the lipophilic bioactive compound is stabilized against oxidation and/or photochemical degradation, characterized in that the composition comprises a micellar solution of non-aqueous alkoxylated solvent micelles in an aqueous solution, and where the non-aqueous alkoxylated solvent micelles encapsulate the lipophilic bioactive compound and where the non-aqueous alkoxylated solvent has a formula:

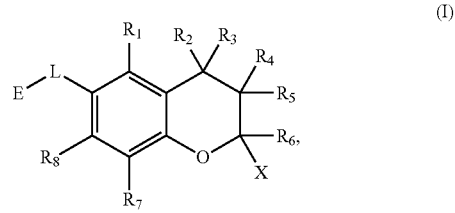

(I)

where L corresponds to linker segment or a chemical bond, E corresponds to an alkoxylated segment having a formula comprising repeats of —O—R—, where R corresponds to an linear or branched alkyl C2 to C5 chain, X corresponds to a linear or branched alkyl chain, and R1, R2, R3, R4, R5, R7, R8 independently of each other correspond to either H or CH3.

It is a further object of the present invention to provide a process for stabilising a lipophilic bioactive compound such as a cannabinoid, in particular a phytocannabinoid or a synthetic cannabinoid, against oxidation and/or photochemical degradation, comprising the steps of, in this order:

a. heating an amount of a non-aqueous alkoxylated solvent having the formula (I),

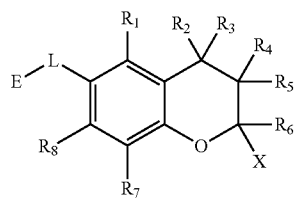

(I)

where L corresponds to linker segment or a chemical bond, E corresponds to an alkoxylated segment having a formula comprising repeats of —O—R—, where R corresponds to an linear or branched alkyl C2 to C5 chain, X corresponds to a linear or branched alkyl chain, and R1, R2, R3, R4, R5, R7, R8 independently of each other correspond to either H or CH3 to a first temperature such as to form a melt of the non-aqueous alkoxylated solvent, b. adding an amount of lipophilic bioactive compound such as a cannabinoid to the melt of the non-aqueous alkoxylated solvent and mixing such as to dissolve the lipophilic bioactive compound such as a cannabinoid in the melt of the non-aqueous alkoxylated solvent and thereby forming a first homogenous liquid mixture, while maintaining a first mixing temperature of the first homogenous liquid mixture within 10° C. of the first temperature with the proviso that the first mixing temperature corresponds at least to the melting temperature of non-aqueous alkoxylated solvent, c. adding an amount of an aqueous solution, preferably an aqueous solution of a of a carboxylic acid having two or more carboxyl moieties to the first homogenous liquid mixture, wherein the temperature of the aqueous solution, preferably an aqueous solution of a of a carboxylic acid having two or more carboxyl moieties, is within 10° C. of the first temperature with the proviso that the temperature corresponds at least to the melting temperature of the non-aqueous alkoxylated solvent, and mixing such as to form a micellar solution of non-aqueous alkoxylated solvent micelles encapsulating the lipophilic bioactive compound in the aqueous solution, preferably in the aqueous solution of a carboxylic acid having two or more carboxyl moieties, d. reducing the temperature of the micellar solution to a temperature below the melting temperature of the non-aqueous alkoxylated solvent.

It is yet a further object of the present invention to provide a process for stabilizing a lipophilic bioactive compound such as a cannabinoid, in particular a phytocannabinoid or a synthetic cannabinoid, against oxidation and/or photochemical degradation, against oxidation and/or photochemical degradation, comprising the steps of, in this order:

a. heating an amount of a non-aqueous alkoxylated solvent having the formula (I),

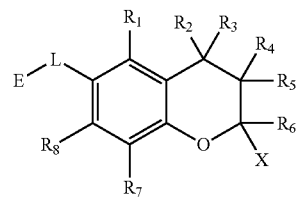

(I)

where L corresponds to linker segment or a chemical bond, E corresponds to an alkoxylated segment having a formula comprising repeats of —O—R—, where R corresponds to an linear or branched alkyl C2 to C5 chain, X corresponds to a linear or branched alkyl chain, and R1, R2, R3, R4, R5, R7, R8 independently of each other correspond to either H or CH3, to a first temperature of preferably between 35 and 79° C., more preferably between 40 and 55° C., such as to form a melt of the non-aqueous alkoxylated solvent, b. adding an amount of a non-aqueous non-alkoxylated solvent having the formula (II):

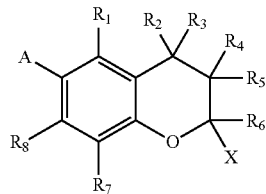

(II)

where A corresponds to H, SH, NH2, COOH, CONH2 or OH or a C1-C8 alkyl segment or C2-C8 alkenyl segment at least bearing one H, SH, NH2, COOH, CONH2 or OH, X corresponds to a linear or branched alkyl or alkenyl chain, and R1, R2, R3, R4, R5, R7, R8 independently of each other correspond to either H or CH3 to the melt of the non-aqueous alkoxylated solvent and mixing such as to dissolve the non-aqueous non-alkoxylated solvent in the melt of the non-aqueous alkoxylated solvent and thereby forming a first homogenous liquid mixture, while maintaining the temperature of the first homogenous liquid mixture within 10° C. of the first temperature with the proviso that the temperature corresponds at least to the melting temperature of the non-aqueous alkoxylated solvent, c. adding an amount of lipophilic bioactive compound such as a cannabinoid to the first homogenous liquid mixture and mixing such as to dissolve the lipophilic bioactive compound such as a cannabinoid in the first homogenous liquid mixture and thereby forming a second homogenous liquid mixture, while maintaining a second mixing temperature of the second homogenous liquid mixture within 10° C. of the first temperature with the proviso that the second mixing temperature corresponds at least to the melting temperature of the non-aqueous alkoxylated solvent, d. adding an amount of an aqueous solution, preferably an aqueous solution of a carboxylic acid having two or more carboxyl moieties to the second homogenous liquid mixture, wherein a third mixing temperature of the aqueous solution of a carboxylic acid having two or more carboxyl moieties is within 10° C. of the first temperature with the proviso that the third mixing temperature corresponds at least to the melting temperature of non-aqueous alkoxylated solvent, and mixing such as to form a micellar solution of non-aqueous alkoxylated solvent and non-aqueous non-alkoxylated solvent micelles
encapsulating the cannabinoid in the aqueous solution of a carboxylic acid having two or more carboxyl moieties,
e. reducing the temperature of the micellar solution to a temperature below the melting temperature of non-aqueous alkoxylated solvent and non-aqueous non-alkoxylated solvent and optionally maintaining the temperature of the micellar solution until the micellar solution is optically transparent.

It is yet a further object of the present invention to provide a use of a composition according to the above object for reducing oxidation and/or photochemical degradation of a lipophilic bioactive compound such as a cannabinoid.

It is yet a further object of the present invention to provide a process for use of a composition according to the above object in a pharmaceutical formulation, preferably in an oral or topical pharmaceutical formulation.

Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings, FIG. 1 shows the THC content in different stabilizing systems. The upper data set, which is nearly flat over time, shows the evolution of the relative concentration of tetrahydrocannabinol (THC) in a system including 1 weight percent tocopherol. The lower data set, which is declining with time, shows the evolution of the relative concentration of tetrahydrocannabinol (THC) in a system including no tocopherol. In the lower data set, the initial concentration of THC is reduced to 91% at day 93 with respect to the initial concentration of THC at day 0.

DESCRIPTION OF PREFERRED EMBODIMENTS

It is understood that the compounds used in the composition, in particular the lipophilic bioactive compound, non-aqueous alkoxylated solvent and non-aqueous non-alkoxylated solvent and others may be of pharmaceutically acceptable grade, i.e. pharmaceutically acceptable.

It is understood that the process according to the present invention, during steps a. to d. or e., the formed melts and mixtures liquids or gels are processed by agitating the melts, liquids or gels such as to ensure thorough mixing and formation of homogenous solutions or mixtures.

It a first aspect, the present invention to provides a stabilized composition comprising a lipophilic bioactive compound such as a cannabinoid, in particular a phytocannabinoid or a synthetic cannabinoid, where the lipophilic bioactive compound is stabilized against oxidation and/or photochemical degradation, characterized in that the composition comprises a micellar solution of non-aqueous alkoxylated solvent micelles in an aqueous solution, and where the non-aqueous alkoxylated solvent micelles encapsulate the lipophilic bioactive compound and where the non-aqueous alkoxylated solvent has a formula:

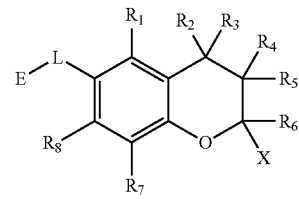

(I)

where L corresponds to linker segment or a chemical bond, E corresponds to an alkoxylated segment having a formula comprising repeats of —O—R—, where R corresponds to an linear or branched alkyl C2 to C5 chain, X corresponds to a linear or branched alkyl chain, and R1, R2, R3, R4, R5, R7, R8 independently of each other correspond to either H or CH3.

In a preferred embodiment, the composition according to the present invention is in the
form of a liquid or a gel comprising a micellar solution of non-aqueous alkoxylated solvent micelles in an aqueous solution, and where non-aqueous alkoxylated solvent micelles encapsulate the lipophilic bioactive compound such as a cannabinoid. Encapsulating in micelles the lipophilic bioactive compound helps on one hand to solubilize the lipophilic bioactive compound in aqueous environments and on the other hand helps stabilizing the lipophilic bioactive compound such as a cannabinoid against degradation, and no further organic solvents are needed to increase the content of the lipophilic bioactive compound such as a cannabinoid.

In a preferred embodiment, the composition further comprises a non-aqueous non-alkoxylated solvent and the composition comprises a micellar solution of non-aqueous alkoxylated solvent and non-aqueous non-alkoxylated solvent micelles in an aqueous solution, and where the non-aqueous alkoxylated solvent and non-aqueous non-alkoxylated solvent micelles encapsulate the lipophilic bioactive compound such as a cannabinoid and where the non-aqueous non-alkoxylated solvent has a formula:

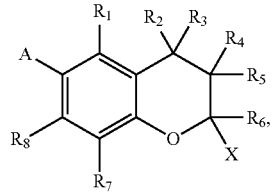

(II)

where A corresponds to H, SH, NH$_2$, COOH, CONH$_2$ or OH or a C1-C8 alkyl segment or C2-C8 alkenyl segment at least bearing one H, SH, NH$_2$, COOH, CONH$_2$ or OH, X corresponds to a linear or branched alkyl or alkenyl chain, and R$_1$, R$_2$, R$_3$, R$_4$, R$_5$, R$_7$, R$_8$ independently of each other correspond to either H or CH$_3$.

In a preferred embodiment, in the composition according to the present invention, the lipophilic bioactive compound may be chosen from lipophilic bioactive compounds that are isolated from plants or animals and in particular such lipophilic bioactive compounds which are light-sensitive. This includes compounds such as lipophilic vitamins such as vitamin A, flavonoids, cannabinoids, ubiquinol/ubiquinone, phytosterols, phytoestrogens, polyphenols, anthocyanins, omega-3 fatty acids, carotenoids such as lutein, astaxanthine, beta-carotene. Alternatively, the lipophilic bioactive compound may be an active pharmaceutical ingredient. In particular, the lipophilic bioactive compound may be chosen among cannabinoids such as cannabidiol or tetrahydrocannabinol. Cannabidiol (CBD) is one of at least 113 active cannabinoids identified in cannabis. It is a major phytocannabinoid, accounting for up to 40% of the plant's extract and has been considered to have a wide scope of potential medical applications—due to clinical reports showing the lack of side effects, particularly a lack of addictive potential. It is notorious for being particularly instable when exposed to light and/or heat and is therefore stored as crystalline solid since solutions cannot be stored for more than a few days. Cannabidiol is furthermore sparingly soluble in aqueous solutions, which is why solubility and hence, bioavailability, can be increased by providing a micellar solution of micelles encapsulating the cannabidiol in an aqueous solution. The same can be said of tetrahydrocannabinol.

In a preferred embodiment, in the composition according to the present invention, the non-aqueous non-alkoxylated solvent is a tocopherol such as alpha-, beta-, gamma- or delta-tocopherol or tocotrienol such as alpha-, beta-, gamma- or delta-tocotrienol. Tocopherol and tocotrienol are readily available commercially from sources such vegetable oils, nuts and seeds. While they help the formation of micelles that are particularly stable, furthermore some of the tocopherols and/or tocotrienols useful in the present invention also have vitamin E activity. Without wishing to be bound to a particular theory, it is believed that the use of tocopherols, which are structurally similar to cannabinoids in particular, in conjunction with one or more non-aqueous alkoxylated solvent provides for the stabilization effect observed in the compositions according to the present invention.

In a preferred embodiment, in the composition according to the present invention, the lipophilic bioactive compound such as a cannabinoid is present in an amount of 0.1-10 weight percent, preferably of 0.1 to 7 weight respect, with respect to the total weight of the composition.

In a preferred embodiment, in the composition according to the present invention, the lipophilic bioactive compound such as a cannabinoid is present in an amount of 0.1-10 weight percent, preferably of 0.1 to 7 weight percent, with respect to the total weight of the composition, and the non-aqueous alkoxylated solvent and non-aqueous non-alkoxylated solvent may be present in an amount of 5 to 50 weight percent and more preferably of 10 to 20 weight percent with respect to the total weight of the composition, whereas the remainder is formed by an aqueous solution, preferably an aqueous solution of a carboxylic acid having two or more carboxyl moieties.

While the composition according to the present invention are able to accommodate lipophilic bioactive compounds in an amount of 0.1-10 weight percent, with respect to the total weight of the composition, the amount of cannabinoids is usually in the range of of 0.1-3 weight percent, the amount of krill oil and/or astaxanthin is usually in the range of 0.1-6.5 weight percent, the amount of graviola plant extract is usually in the range of of 0.1-8 weight percent, the amount of curcuma plant extract is usually in the range of 0.5-4 weight percent, the amount of ubichinone is usually in the range of 0.1-5 weight percent and the amount of propolis and Siberian ginseng plant extract is usually in the range of 0.1-4 weight percent.

In a preferred embodiment, in the composition according to the present invention, the weight ratio between the non-aqueous alkoxylated and the non-aqueous non-alkoxylated solvent is of from 5:1 to 199:1 and preferably is from 19:1 to 99:1. This ratio allows formation of stable composite micelles of non-aqueous non-alkoxylated and non-aqueous alkoxylated solvent that further allow for good bioavailability of the lipophilic bioactive compound such as a cannabinoid. For example, in the case where the non-aqueous non-alkoxylated solvent is a tocopherol and the non-aqueous alkoxylated solvent is TPGS, the weight ratio between the TPGS and the tocopherol can be within the above range such as for example approximately 19:1, 49:1, 99:1.

In a preferred embodiment, in the composition according to the present invention, the aqueous solution may be formed by an aqueous solution of a carboxylic acid having two or more carboxyl moieties or a salt thereof. In particular, the aqueous solution of a carboxylic acid having two or more carboxyl moieties or a salt thereof may further comprise one or more carboxylic acids having one carboxyl moiety or a salt thereof. Examples of a suitable carboxylic acid having two or more carboxyl moieties or a salt thereof are acids such as tricarboxylic acids like citric acid or its mono-, di- or tri-salts.

In a second aspect, the present invention provides a process for stabilising a lipophilic bioactive compound such as a cannabinoid, in particular a phytocannabinoid or a synthetic cannabinoid, against oxidation and/or photochemical degradation, comprising the steps of, in this order:
   a. heating an amount of a non-aqueous alkoxylated solvent having the formula

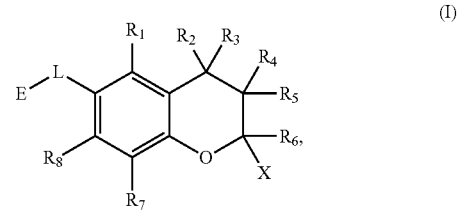

(I)

where L corresponds to linker segment or a chemical bond, E corresponds to an alkoxylated segment having a formula comprising repeats of —O—R—, where R corresponds to an linear or branched alkyl C2 to C5 chain, X corresponds to a linear or branched alkyl chain, and $R_1$, $R_2$, $R_3$, $R_4$, $R_5$, $R_7$, $R_8$ independently of each other correspond to either H or $CH_3$ to a first temperature such as to form a melt of the non-aqueous alkoxylated solvent,
   b. adding an amount of lipophilic bioactive compound such as a cannabinoid to the melt of the non-aqueous alkoxylated solvent and mixing such as to dissolve the lipophilic bioactive compound such as a cannabinoid in the melt of the non-aqueous alkoxylated solvent and thereby forming a first homogenous liquid mixture, while maintaining a first mixing temperature of the first homogenous liquid mixture within 10° C. of the first temperature with the proviso that the first mixing temperature corresponds at least to the melting temperature of non-aqueous alkoxylated solvent,
   c. adding an amount of an aqueous solution, preferably an aqueous solution of a carboxylic acid having two or more carboxyl moieties to the first homogenous liquid mixture, wherein the temperature of the aqueous solution, preferably an aqueous solution of a carboxylic acid having two or more carboxyl moieties, is within 10° C. of the first temperature with the proviso that the temperature corresponds at least to the melting temperature of the non-aqueous alkoxylated solvent, and mixing such as to form a micellar solution of non-aqueous alkoxylated solvent micelles encapsulating the lipophilic bioactive compound in the aqueous solution, preferably in the aqueous solution of a carboxylic acid having two or more carboxyl moieties, d. reducing the temperature of the micellar solution to a temperature below the melting temperature of the non-aqueous alkoxylated solvent and optionally maintaining the temperature of the micellar solution until the micellar solution is optically transparent.

In a third aspect, the present invention provides a process for stabilising a lipophilic bioactive compound such as a cannabinoid, in particular a phytocannabinoid or a synthetic cannabinoid, against oxidation and/or photochemical degradation, against oxidation and/or photochemical degradation, comprising the steps of, in this order:

a. heating an amount of a non-aqueous alkoxylated solvent having the formula

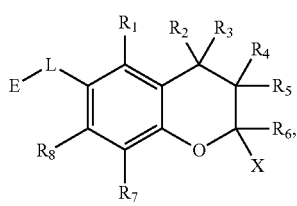

(I)

where L corresponds to linker segment or a chemical bond, E corresponds to an alkoxylated segment having a formula comprising repeats of —O—R—, where R corresponds to an linear or branched alkyl C2 to C5 chain, X corresponds to a linear or branched alkyl chain, and $R_1$, $R_2$, $R_3$, $R_4$, $R_5$, $R_7$, $R_8$ independently of each other correspond to either H or $CH_3$ to a first temperature of preferably between 35 and 70° C., more preferably between 40 and 55° C., such as to form a melt of the non-aqueous alkoxylated solvent, b. adding an amount of a non-aqueous non-alkoxylated solvent having the formula:

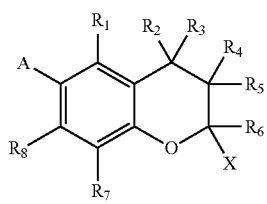

(II)

where A corresponds to H, SH, $NH_2$, COOH, $CONH_2$ or OH or a C1-C8 alkyl segment or C2-C8 alkenyl segment at least bearing one H, SH, $NH_2$, COOH, $CONH_2$ or OH, X corresponds to a linear or branched alkyl or alkenyl chain, and $R_1$, $R_2$, $R_3$, $R_4$, $R_5$, $R_7$, $R_8$ independently of each other correspond to either H or $CH_3$ to the melt of the non-aqueous alkoxylated solvent and mixing such as to dissolve the non-aqueous non-alkoxylated solvent in the melt of the non-aqueous alkoxylated solvent and thereby forming a first homogenous liquid mixture, while maintaining the temperature of the first homogenous liquid mixture within 10° C. of the first temperature with the proviso that the temperature corresponds at least to the melting temperature of the non-aqueous alkoxylated solvent, c. adding an amount of lipophilic bioactive compound such as a cannabinoid to the first homogenous liquid mixture and mixing such as to dissolve the lipophilic bioactive compound such as a cannabinoid in the first homogenous liquid mixture and thereby forming a second homogenous liquid mixture, while maintaining a second mixing temperature of the second homogenous liquid mixture within 10° C. of the first temperature with the proviso that the second mixing temperature corresponds at least to the melting temperature of the non-aqueous alkoxylated solvent, d. adding an amount of an aqueous solution, preferably an aqueous solution of a carboxylic acid having two or more carboxyl moieties to the second homogenous liquid mixture, wherein a third mixing temperature of the aqueous solution of a carboxylic acid having two or more carboxyl moieties is within 10° C. of the first temperature with the proviso that the third mixing temperature corresponds at least to the melting temperature of non-aqueous alkoxylated solvent, and mixing such as to form a micellar solution of non-aqueous alkoxylated solvent and non-aqueous non-alkoxylated solvent micelles encapsulating the cannabinoid in the aqueous solution of a carboxylic acid having two or more carboxyl moieties, e. reducing the temperature of the micellar solution to a temperature below the melting temperature of non-aqueous alkoxylated solvent and non-aqueous non-alkoxylated solvent and optionally maintaining the temperature of the micellar solution until the micellar solution is optically transparent.

The lipophilic bioactive compounds can thus be protected against oxidation and/or photochemical degradation by stabilizing them in the form of a micellar solution of non-aqueous alkoxylated and non-aqueous non-alkoxylated solvent micelles encapsulating the lipophilic bioactive compounds in an aqueous solution. The thus stabilized lipophilic bioactive compounds exhibit good shelf life at room temperature and further eliminate the need for including a protective gas in the container in which the stabilized lipophilic bioactive compounds are stored.

The process for stabilising a lipophilic bioactive compound according to the present invention may be carried out in suitable vessels equipped with temperature-control means as well as mixing means, such as for example a magnetic stirrer.

In a preferred embodiment of the processes for stabilising a lipophilic bioactive compound, the step e. of reducing the temperature of the micellar solution to a temperature below the melting temperature of non-aqueous alkoxylated solvent and non-aqueous non-alkoxylated solvent may be carried out concomitantly with step d., and in particular after the addition of the aqueous solution of a carboxylic acid and concomitantly with the ensuing mixing sub-step.

In a fourth aspect, the present invention also provides a pharmaceutical formulation comprising a composition according to the first aspect of the present invention. The pharmaceutical formulation may be chosen mainly, but not exclusively, from oral or topical formulations.

In particular, when the composition is provided in an oral formulation, the composition may be used as-is or may be combined with other excipients such as for example flavoring agents, antioxidants and so on. The oral formulation may be a liquid or sirup, gel or encapsulated gel. When the composition is provided in a topical formulation, the composition may be used as-is or may be combined with other excipients such as for example oil or in general emollients, stabilizers and so on. The topical formulation may be a cream, gel, liniment or balm, lotion, or ointment, etc. In an alternative embodiment, the topical formulation comprising the composition is a transdermal patch of a lipophilic bioactive compound such as a cannabinoid, which preferably continuously releases the lipophilic bioactive compound such as a cannabinoid through the skin and into the bloodstream, i.e. is a transdermal patch providing extended release of a lipophilic bioactive compound such as a cannabinoid.

In a fifth aspect, the present invention thus provides a use of a composition according to the first aspect of the present invention for reducing oxidation and/or photochemical degradation of a lipophilic bioactive compound such as a cannabinoid. The composition can thus be used for providing lipophilic bioactive compounds such as a cannabinoid where the lipophilic bioactive compound such as a cannabinoid is stabilized in a micelle formed from non-aqueous alkoxylated and non-aqueous non-alkoxylated solvent and in which the compound is protected from the influence of radiation, especially natural light and photooxidation.

In a sixth aspect, the present invention thus provides a use of a composition according to the first aspect of the present invention in a pharmaceutical formulation such as for example a topical oral formulation.

Further embodiments of the invention are laid down in the dependent claims.

EXAMPLES 18 parts by weight of vitamin E polyethylene glycol succinate was placed in a beaker and heated to a temperature of between 70 and 80° C. until a first pale yellow and transparent melt was formed. To this melt, 1 parts by weight of a DL-alpha-tocopherol (commercially obtainable from BASF Germany) was added to the first melt while maintaining a temperature of between 40 and 55° C. until a second slightly yellow and transparent melt was formed. Subsequently, 1 part by weight of a cannabidiol as natural extract or synthetic ingredient was added to the second melt while maintaining a temperature of between 40 and 55° C. until the cannabidiol was dissolved, thereby forming a third lightly yellowishtransparent melt. Then, 80 parts by weight of an aqueous solution containing 0.1 parts by weight of potassium sorbate and 0.05 parts by weight of citric acid was preheated to a temperature of between 40 and 55° C. was added to the third melt under agitation such as to disperse the water within the third melt and form a slightly yellow and transparent gel which was then cooled to 4° C. to form a stabilized composition comprising cannabidiol.

The invention claimed is:

1. A composition comprising a cannabinoid as a lipophilic bioactive compound, wherein the cannabinoid is stabilized against oxidation and/or photochemical degradation,
  characterized in that the composition comprises a micellar solution of composite micelles of non-aqueous alkoxylated solvent and non-aqueous non-alkoxylated solvent in an aqueous solution,
  wherein the composite micelles encapsulate the cannabinoid,
  wherein the non-aqueous alkoxylated solvent is alpha-, beta-, gamma- or delta-tocopherol polyethylene glycol succinate,
  wherein the non-aqueous non-alkoxylated solvent is alpha-, beta-, gamma- or delta-tocopherol, or is alpha- beta-, gamma- or delta-tocotrienol,
  wherein a weight ratio between the non-aqueous alkoxylated solvent and the non-aqueous non-alkoxylated solvent is of from 5:1 to 99:1,
  wherein the non-aqueous alkoxylated solvent is present in an amount of 10 to 20 weight percent with respect to a total weight of the composition,
  wherein the cannabinoid is present in an amount of 0.1 to 2 weight percent, with respect to the total weight of the composition.

2. The composition according to claim 1, wherein the cannabinoid is cannabidiol or dronabinol.

3. A pharmaceutical formulation comprising a composition according to claim 1, wherein the pharmaceutical formulation is an oral or topical pharmaceutical formulation.

4. A process for stabilising a lipophilic bioactive compound, against oxidation and/or photochemical degradation, against oxidation and/or photochemical degradation, comprising the steps of, in this order:
  a. heating an amount of a non-aqueous alkoxylated solvent to a first temperature between 35 and 70° C., such as to form a melt of the non-aqueous alkoxylated solvent,
  b. adding an amount of a non-aqueous non-alkoxylated solvent to the melt of the non-aqueous alkoxylated solvent and mixing such as to dissolve the non-aqueous non-alkoxylated solvent in the melt of the non-aqueous alkoxylated solvent and thereby forming a first homogenous liquid mixture, while maintaining the temperature of the first homogenous liquid mixture within 10° C. of the first temperature with the proviso that the temperature corresponds at least to the melting temperature of the non-aqueous alkoxylated solvent,
  c. adding an amount of lipophilic bioactive compound to the first homogenous liquid mixture and mixing such as to dissolve the lipophilic bioactive compound in the first homogenous liquid mixture and thereby forming a second homogenous liquid mixture, while maintaining a second mixing temperature of the second homogenous liquid mixture within 10° C. of the first temperature with the proviso that the second mixing temperature corresponds at least to the melting temperature of the non-aqueous alkoxylated solvent,
  d. adding an amount of an aqueous solution to the second homogenous liquid mixture, wherein a third mixing temperature of the aqueous solution is within 10° C. of the first temperature with the proviso that the third mixing temperature corresponds at least to the melting temperature of non-aqueous alkoxylated solvent, and mixing such as to form a micellar solution of non-aqueous alkoxylated solvent and non-aqueous non-alkoxylated solvent micelles encapsulating the lipophilic bioactive compound in the aqueous solution,
  e. reducing the temperature of the micellar solution to a temperature below the melting temperature of non-aqueous alkoxylated solvent and non-aqueous non-alkoxylated solvent,
  wherein the lipophilic bioactive compound is a cannabinoid, and the non-aqueous alkoxylated solvent is alpha-, beta-, gamma- or delta-tocopherol polyethylene glycol succinate,
  wherein the non-aqueous non-alkoxylated solvent is alpha-, beta-, gamma- or delta-tocopherol, or is alpha- beta-, gamma- or delta-tocotrienol, wherein a weight ratio between the non-aqueous alkoxylated solvent and the non-aqueous non-alkoxylated solvent is of from 5:1 to 99:1,
wherein the non-aqueous alkoxylated solvent is present in an amount of 10 to 20 weight percent with respect to a total weight of the composition, and
wherein the cannabinoid is present in an amount of 0.1 to 2 weight percent, with respect to the total weight of the composition.

5. The process according to claim 4, wherein in step a., the first temperature is between 40 and 55° C.

6. The process according to claim 4, wherein in step d., and e., respectively, the temperature of the micellar solution is maintained until the micellar solution is optically transparent.

7. The process according to claim 4, wherein after step a. and before b., the process further comprises the step of adding an amount of a polyol, to the melt of the non-aqueous alkoxylated solvent, and mixing such as to dissolve the polyol in the melt of the non-aqueous alkoxylated solvent, while maintaining a temperature such as to keep the non-aqueous alkoxylated solvent in a molten state.

\* \* \* \* \*